(12) United States Patent
Duric

(10) Patent No.: US 9,360,449 B2
(45) Date of Patent: Jun. 7, 2016

(54) FUNCTIONAL MONITORING OF AN ELECTROLYTIC GAS SENSOR HAVING THREE ELECTRODES, AND HAZARD ALARM AND GAS MEASURING DEVICE

(71) Applicant: SIEMENS AKTIENGESELLSCHAFT, Munich (DE)

(72) Inventor: Aleksandar Duric, Zug (CH)

(73) Assignee: Siemens Aktiengesellschaft, Munich (DE)

( * ) Notice: Subject to any disclaimer, the term of this patent is extended or adjusted under 35 U.S.C. 154(b) by 176 days.

(21) Appl. No.: 14/310,107

(22) Filed: Jun. 20, 2014

(65) Prior Publication Data

US 2014/0375463 A1 Dec. 25, 2014

(30) Foreign Application Priority Data

Jun. 20, 2013 (EP) .................................. 13172931

(51) Int. Cl.
*G08B 21/00* (2006.01)
*G01N 27/416* (2006.01)
*G08B 21/14* (2006.01)

(52) U.S. Cl.
CPC ............ *G01N 27/4163* (2013.01); *G08B 21/14* (2013.01)

(58) Field of Classification Search
CPC . G01N 27/4163; G01N 27/4161; G08B 21/14
USPC ........................................................ 340/632
See application file for complete search history.

(56) References Cited

U.S. PATENT DOCUMENTS

| 4,777,444 | A | 10/1988 | Beijk et al. |
| 5,100,530 | A | 3/1992 | Dörr et al. |
| 5,202,637 | A | 4/1993 | Jones |
| 5,372,133 | A * | 12/1994 | Hogen Esch ......... A61B 5/0031 128/903 |
| 6,428,684 | B1 | 8/2002 | Warburton |
| 8,594,760 | B2 | 11/2013 | Wieder et al. |
| 8,974,386 | B2 * | 3/2015 | Peyser ................. A61B 5/0031 600/309 |
| 9,078,607 | B2 * | 7/2015 | Heller ................ A61B 5/14532 600/345 |
| 2007/0163894 | A1 * | 7/2007 | Wang ................... A61B 5/1495 205/792 |
| 2009/0057148 | A1 * | 3/2009 | Wieder .............. A61B 5/14532 204/403.01 |

FOREIGN PATENT DOCUMENTS

| EP | 0241601 A1 | 10/1987 |
| EP | 0417347 A1 | 3/1991 |
| EP | 2030561 A1 | 3/2009 |
| JP | H04190154 A | 7/1992 |

* cited by examiner

*Primary Examiner* — Mark Rushing
(74) *Attorney, Agent, or Firm* — Laurence Greenberg; Werner Stemer; Ralph Locher

(57) ABSTRACT

An electrolytic gas sensor which is sensitive to a specific gas and has a working, reference and counter electrode is functionally monitored. A differential voltage between the reference and working electrodes is amplified and the potential of the counter electrode is regulated to minimize the differential voltage. Then a measured current flowing into the counter electrode approximately proportionally to the gas concentration of the gas to be detected arises. Independently of the determination of the gas concentration, a working, counter and reference voltage which is present at the three electrodes in each case is captured and monitored for an impermissible deviation. In an impermissible case an assigned error message is then output. Online monitoring of the gas sensor is thus possible and no interruption of the measurement operation for test purposes and additional components are required.

12 Claims, 5 Drawing Sheets

FUNCTIONAL MONITORING OF AN ELECTROLYTIC GAS SENSOR HAVING THREE ELECTRODES, AND HAZARD ALARM AND GAS MEASURING DEVICE

CROSS-REFERENCE TO RELATED APPLICATION

This application claims the priority, under 35 U.S.C. §119, of European patent application EP 13172931, filed Jun. 20, 2013; the prior application is herewith incorporated by reference in its entirety.

BACKGROUND OF THE INVENTION

Field of the Invention

The present invention relates to a method and an apparatus for the functional monitoring of an electrolytic gas sensor which is sensitive to a specific gas, having three electrodes, in particular a working, reference and counter electrode, for electrical faults such as short circuits, short circuits to ground and interruptions of the individual electrodes or combinations thereof.

For the meteorological determination of a gas concentration it is in this case known for a differential voltage present between the reference and working electrodes to be amplified. On this basis the potential of the counter electrode is then regulated such that the differential voltage becomes as small as possible. In this case a measured current flowing into the counter electrode approximately proportionally to the gas concentration of the gas to be detected arises.

From the prior art numerous methods are known which permit monitoring of the gas sensor, by applying e.g. a voltage pulse or a series of pulses to the electrodes of the gas sensor and by subsequently measuring different electrical characteristics.

United States patent application No. US 2009/0107838 A1 describes an electrochemical carbon monoxide gas sensor, in which a voltage pulse is applied to the counter electrode. Then the current into the working electrode is measured and analyzed.

European published patent application EP 1039293 A1 describes a method for the inspection of an electrochemical gas sensor, in which a voltage with reverse polarity is applied between working and counter electrode, so that hydrogen and oxygen are produced. After return to measurement operation the previously generated gas acts as a stimulus for the sensor. In this way the functionality and any aging of the gas sensor can be established. However, this method is not suitable if the access opening of the gas sensor is blocked.

International patent application publication WO 99/18430 A1 describes a monitoring method for electrochemical sensors, in which an alternating current with a small amplitude is applied to the sensor electrode. The impedance between the individual electrodes is then measured, in order therefrom to assess the status of the sensor.

The invention further relates to a hazard alarm which has at least one electrolytic gas sensor, in each case sensitive to a specific gas, and such an apparatus for functional monitoring. The hazard alarm is preferably a gas alarm, in particular a CO gas alarm or carbon monoxide gas alarm. The hazard alarm has a first output unit for outputting a warning or alarm message if a determined respective gas concentration exceeds a predefined threshold value or a threshold value which is time-dependent on the respective gas concentration. It has a second output unit for outputting an error message in the event that a malfunction of the respective gas sensor is determined.

Such hazard alarms, typically embodied as point alarms, are used to identify at an early stage an undesired occurrence of a hazard situation such as for example an escape and/or an occurrence of a hazardous gas such as carbon monoxide. They are typically accommodated in a hazard-monitored area, e.g. at suitable places within a building. The hazard alarm can also have further detection units for hazard detection, e.g. an optical detection unit working in accordance with the scattered light method for detection of smoke particles or a temperature detection unit for detection of heat in the event of a fire. Such a hazard alarm is also called a multi criteria hazard alarm. The respective detection signals are combined with one another to reduce false alarms and for the more reliable output of a detected hazard.

Such a hazard alarm can also be part of a hazard alarm system or a comprehensive building management system, which besides a control unit also has several hazard alarms embodied as peripheral devices. The peripheral devices can be connected directly or indirectly to the control unit via a wired or wireless communication connection.

Finally the invention relates to a gas measuring device having at least one electrolytic gas sensor, in each case sensitive to a specific gas, and having such an apparatus for the functional monitoring of the respective gas sensor. The gas measuring device has a measurement output unit for outputting a respective gas concentration and a second output unit for outputting an error message in the event of a malfunction of the respective gas sensor being determined.

SUMMARY OF THE INVENTION

It is accordingly an object of the invention to provide a method for the functional monitoring of an electrolytic gas sensor that overcomes the above-mentioned disadvantages of the heretofore-known devices and methods of this general type and which is reliable and particularly simple to implement and which impedes the sensor operation as little as possible.

With the foregoing and other objects in view there is provided, in accordance with the invention, a method for the functional monitoring of an electrolytic gas sensor that is sensitive to a specific gas, the gas sensor having a working electrode, a reference electrode, and a counter electrode, the method comprising:

amplifying a differential voltage present between the reference and working electrodes and regulating the differential voltage on a basis of a potential of the counter electrode such that the differential voltage becomes as small as possible, whereupon a measured current arises which flows into the counter electrode and is approximately proportional to a gas concentration of the gas to be detected; and independently of a determination of the measured current representing the gas concentration, capturing a working voltage present at the working electrode, a counter voltage present at the counter electrode, and a reference voltage present at the reference electrode and monitoring the voltages for an impermissible deviation; and when an impermissible deviation is detected, outputting an assigned error message.

In other words, according to the invention a working, counter and reference voltage present at the three electrodes is captured, independently of the determination of the measured current which represents the gas concentration, and in each case is monitored for an impermissible deviation. In an impermissible case an assigned error message is then output.

The values of the captured working, counter and reference voltages can moreover in each case be mathematically evaluated, e.g. weighted. The respective mathematical evaluations are then monitored for a respective impermissible deviation and in an impermissible case an assigned error message is then output.

This means that advantageously "online" monitoring of the electrochemical gas sensor is possible. Any other interruption of the measurement operation, in which voltage pulses, pulse sequences or small alternating voltages are applied to the electrodes for test purposes can be dispensed with. "Online" monitoring means that all electrode voltages are captured and evaluated at least approximately simultaneously.

In addition, components additionally required for the implementation of the test operation, e.g. an alternating voltage source in the case of the above-mentioned international publication WO 99/18430 A1, can advantageously be dispensed with. In comparison with the above-mentioned published application US 2009/0107838 A1 no subsequent recovery time must be adhered to after a pulse excitation for the test operation.

Impermissible deviation of a working, counter and reference voltage means the deviation of a currently captured working, counter and reference voltage value from a respectively predetermined comparison voltage value, both "upward" and/or "downward," i.e. if the respective upper comparison voltage value is exceeded and/or if the respective lower voltage value is undershot.

The output of the error message can take place optically, e.g. by means of a light signal. The output can alternatively or additionally take place acoustically, e.g. by means of a warning sound. The error message can alternatively or additionally be output to a higher-level control unit. The error message can alternatively or additionally be output in wired or wireless fashion, e.g. by radio, ultrasound or infrared.

The (first) error message can be a collective message which shows that one of the currently captured working, counter and reference voltages values has impermissibly deviated from a respective predetermined comparison voltage value. In the simplest case this error message is merely binary information. The error message can also be encoded, so that the respective impermissible deviation can also be displayed individually.

In accordance with a preferred variant of the method the measured current is first converted into a measured voltage proportional thereto, wherein this measured voltage then represents the gas concentration approximately proportional thereto. The resulting simpler possible meteorological capture is implemented by means of a transimpedance converter or preferably by means of a transimpedance amplifier.

According to another variant of the method a warning or alarm message is output if the measured voltage representing the gas concentration exceeds or undershoots a predefined threshold value or a threshold value which is time-dependent on the gas concentration. Such threshold values are defined e.g. in Europe in accordance with standard EN 50291 for the detection of carbon monoxide (CO) in domestic premises for gas alarms. According to this, an alarm must be given within 3 minutes when e.g. a CO gas concentration of 330±30 ppm is detected, whereas when e.g. a CO gas concentration of 33±3 ppm is detected an alarm may be given at the earliest after 120 minutes. Similarly, the standard UL 2034 which applies in the USA governs the conditions for giving alarms in the case of CO gas alarms.

Obviously other threshold values can be predefined for other gases to be detected, such as e.g. carbon dioxide ($CO_2$), ethanol or methane. When a single threshold value is reached an alarm can also be given immediately.

According to another variant of the method the measured voltage is monitored for an impermissible voltage deviation. In an impermissible case an assigned second error message is then output. This is e.g. the case should the measured voltage have a negative voltage value or should the measured voltage have a positive voltage value which undershoots or exceeds a predefined minimum or maximum comparison value.

The second error message can also be output if the measured voltage changes abruptly, in which case such a temporal change is not plausible in terms of a physical change in the gas concentration or does not correspond to the sensor response. For example, the change in the output signal of the CO sensor amplifier must not rise from a quiescent value to the maximum value within between 1 and 2 measurement cycles. The same applies to a drop from a maximum value to a quiescent value.

According to another variant of the method at least one combination of the measurement, working, counter and reference voltages is monitored in each case for another impermissible deviation. In an impermissible case an assigned third error message is then output. This may be the monitoring of a differential voltage, e.g. the differential voltage between the reference and counter electrodes, for an impermissible deviation. The combination may be an addition, a subtraction, a weighted addition or subtraction. In principle other mathematical functions can be taken into account for an evaluated combination which permit the reliable or more reliable detection of an error.

With the above and other objects in view there is also provided, in accordance with the invention, an apparatus for the functional monitoring of an electrolytic gas sensor that is sensitive to a specific gas and that has three electrodes including a working electrode, a reference electrode, and a counter electrode, the apparatus comprising:
  a potentiostat for amplifying a differential voltage present between the reference and working electrodes and for regulating a potential of the counter electrode so that the differential voltage becomes as small as possible; and an electronic processing unit configured to capture a measured current that flows into the counter electrode and that is approximately proportional to a gas concentration of the gas to be detected;
  said electronic processing unit being further configured, independently of determining the gas concentration, to capture a working voltage, a counter voltage, and a reference voltage respectively present at the three electrodes, in each case to monitor the respective voltage for an impermissible deviation and, in an impermissible case, to output an assigned error message.

In other words, the objects of the invention are further achieved by an apparatus corresponding to the inventive method for the functional monitoring of an electrolytic gas sensor which is sensitive to a specific gas and which has a working, reference and counter electrode. The apparatus has a potentiostat for amplifying a differential voltage present between the reference and working electrodes and for regulating the potential of the counter electrode so that the differential voltage becomes as small as possible. The apparatus has an electronic processing unit for capturing a measured current flowing into the counter electrode and arising approximately proportionally to a gas concentration of the gas to be detected. The electronic processing unit is additionally set up to capture a working, counter and reference voltage present at the three electrodes in each case, independently of the determination of the gas concentration, to monitor it for an impermissible deviation and in an impermissible case to output an assigned (first) error message.

The mode of operation of a potentiostat in the field of electrolytic gas sensor equipment is sufficiently known from the prior art. The electronic processing unit is preferably a processor-aided electronic processing unit, e.g. a microcontroller. Alternatively the electronic processing unit can also be implemented in "analog" fashion, e.g. using several window comparators for the detection of the respective impermissible deviation and if necessary using one or more downstream logic gates for outputting a digital signal for the error message.

According to a preferred embodiment the apparatus has a transimpedance amplifier for converting the measured current into a measured voltage proportional thereto and the electronic processing unit for capturing the measured voltage which then represents the gas concentration. Thanks to the amplification and impedance conversion the subsequent voltage-based capture of measured values is then considerably simplified.

According to another embodiment the electronic processing unit is set up to monitor the measured voltage for an impermissible voltage deviation and in an impermissible case to output an assigned second error message.

Preferably the measured voltage and the working, counter and reference voltages have a common reference potential. This reference potential is typically the ground.

According to another advantageous embodiment the processing unit has an A/D converter for converting the measured voltage and the working, counter and reference voltages into corresponding digital values. Alternatively the processing unit can also be connected to an A/D converter by way of a data communications link. The A/D converter is preferably embodied to be multichannel, e.g. four- or eight-channel, so that the measured voltage to be captured and the electrode voltages can be captured in parallel, i.e. simultaneously. The processing unit is set up to monitor the digital values in each case for a digital value corresponding to the impermissible deviation and in an impermissible case to output the respective assigned error message.

Preferably the electronic processing unit is a microcontroller. Such components typically already have a multichannel A/D converter as well as other analog and digital inputs and outputs. The digital values which correspond to the respective impermissible deviations are preferably stored as data values in a nonvolatile data memory of the microcontroller. The comparison of the converted digital values, the digital comparison of these for an impermissible deviation and the output of the second error message take place using software-based means, i.e. by means of a suitable computer program executed on the microcontroller.

According to another embodiment the processing unit is set up to monitor at least one combination of in each case two digital values corresponding to the measured, working, counter and reference voltages for another impermissible deviation and in an impermissible case to output an assigned third error message.

According to a preferred embodiment the measured voltage and the working, counter and reference voltages can be converted into the corresponding digital values by means of the A/D converter at least approximately simultaneously with a scanning rate in a range from 0.25 to 4 Hertz. Because the digital conversion of the captured input voltages at the A/D converter and the arithmetical comparison and if necessary the generation of an error message typically take only a few milliseconds, the microcontroller needs a significant electrical power only for these short cyclical phases, whereas in the predominant pause phases it needs only a small negligible quiescent power. This means a hazard alarm can advantageously be operated with a battery for a period of several years.

In another particularly advantageous embodiment the apparatus has a low-pass smoke filter upstream of the A/D converter for filtering the measured voltage with an edge frequency of less than 10 Hertz, in particular of less than 1 Hertz.

By smoothing the measured voltage a comparatively slow power-saving A/D conversion is possible. In contrast, a comparatively high-frequency A/D conversion in the range of several kilohertz with a downstream digital filter needs many times the electrical power in order to eliminate the high proportion of noise in the measured voltage again.

The object of the invention is further achieved by a hazard alarm having at least one electrolytic gas sensor, in each case sensitive to a specific gas. The hazard alarm in this case has an inventive apparatus for the functional monitoring of the respective gas sensor. The hazard alarm further has a first output unit for outputting a warning or alarm message if a respective determined gas concentration exceeds or undershoots a predefined threshold value or a threshold value which is time-dependent on the respective gas concentration. Moreover, it has a second output unit for outputting an error message in the event that a malfunction of the respective gas sensor is determined.

The output of the error message can take place optically, e.g. by means of a flashing LED of the hazard alarm. The output can alternatively or additionally take place acoustically, e.g. by means of a loudspeaker or a buzzer of the hazard alarm. The error message can alternatively or additionally take place via a communication interface of the hazard alarm to a higher-level control unit. The communication interface can be set up for wired output of the error message, e.g. to a connected alarm bus. Alternatively or additionally the communication interface can be set up for wireless output of the error message. In this case the communication interface can be a radio interface, an ultrasound interface or an infrared interface. The two output units can of course also be combined in a common output unit.

The object of the invention is further achieved by a gas measuring device having at least one electrolytic gas sensor, in each case sensitive to a specific gas, and having an inventive apparatus for the functional monitoring of the respective gas sensor. The gas measuring device has a measurement output unit for outputting a respective gas concentration and a second output unit for outputting an error message in the event of a malfunction of the respective gas sensor being determined.

The concentration value can be output as an analog signal, e.g. in the form of an analog current or voltage signal, or as a digital signal, e.g. digitally encoded or pulse-width modulated. In the simplest case the concentration value is a percentage value, a per mille value or a numerical value in ppm (parts per million). The concentration value can be output in assigned fashion for each gas to be detected. The output of the concentration value can take place as a numerical value on a display unit, e.g. on an LCD, of the gas measurement device. Alternatively or additionally it can be output via a communication interface to a (central) measurement station, e.g. via a data cable or wirelessly, e.g. by radio or infrared.

The output of the error message can take place as described above for the hazard alarm. Alternatively or additionally the error message can be output on the display unit of the gas measurement device. The two output units can in turn be combined in a common output unit.

Other features which are considered as characteristic for the invention are set forth in the appended claims.

Although the invention is illustrated and described herein as embodied in a functional monitoring of an electrolytic gas sensor having three electrodes, and hazard alarm and gas measuring device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

DETAILED DESCRIPTION OF THE INVENTION

Figure 1:
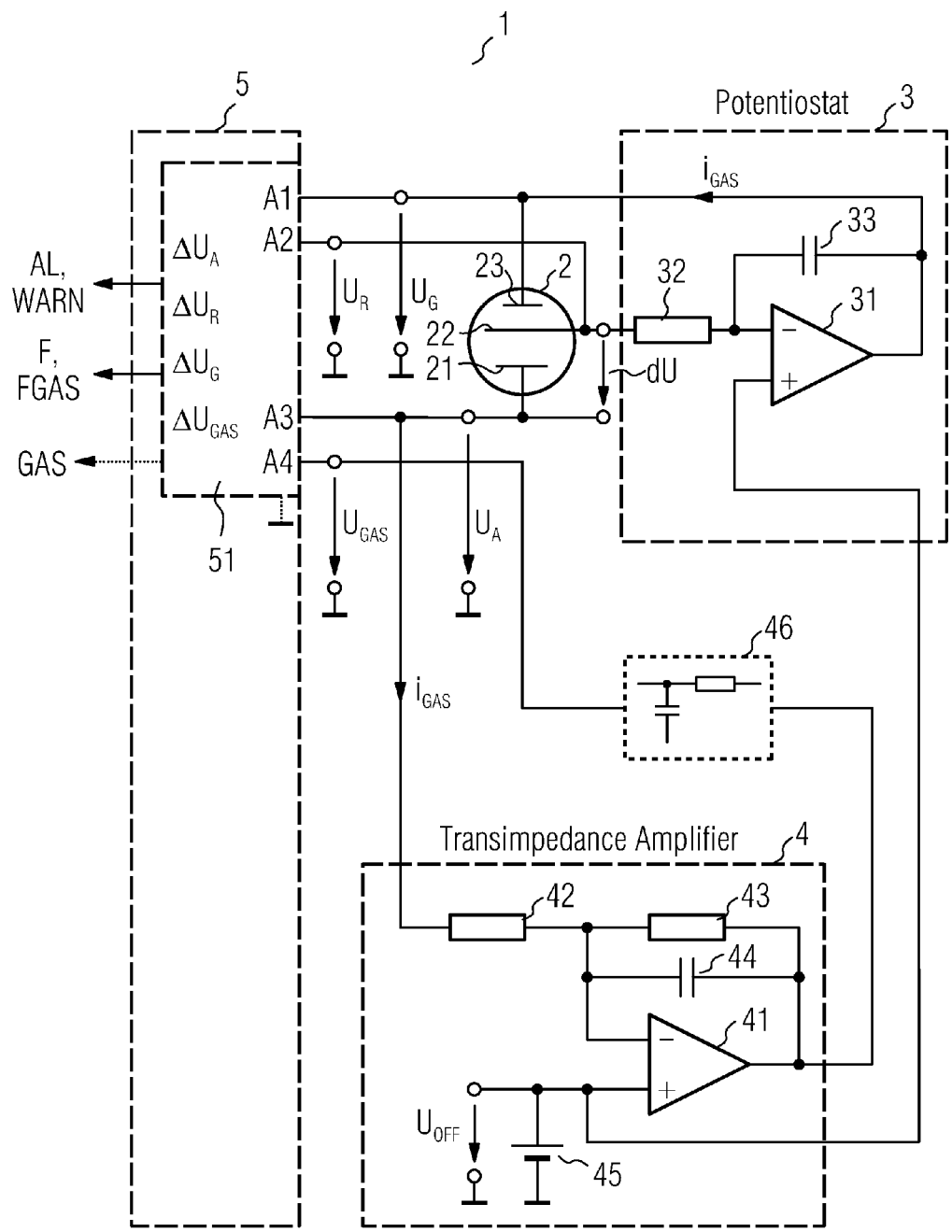
FIG. 1 is a schematic illustrating an example of an apparatus for the functional monitoring of an electrolytic gas sensor having three electrodes according to the invention.

Referring now to the figures of the drawing in detail and first, particularly, to FIG. 1 thereof, there is shown an example of an apparatus 1 for the functional monitoring of an electrolytic gas sensor 2 having three electrodes 21, 22, 23 according to the invention. In the present example the gas sensor 2 to be monitored is already connected to the apparatus 1. The gas sensor 2 is in this case not itself part of the apparatus 1.

The electrolytic gas sensor 2 which is sensitive to a specific gas has a working, reference and counter electrode 21, 22, 23. The gas sensor 2 can be sensitive to e.g. carbon monoxide, methane, hydrogen, ammonia, hydrogen sulfide, nitrogen dioxide, etc. The apparatus 1 further has a potentiostat 3 known from electrolytic gas analysis, which is provided for amplifying a differential voltage dU present between the reference and working electrodes 22, 21 and for regulating the potential of the counter electrode 23, so that the differential voltage dU becomes as small as possible. The potentiostat 3 comprises an operation amplifier 31, the output of which is connected via a capacitor 33 to the latter's inverting input. The inverting input is moreover connected via a resistor 32 to the reference electrode 22. On the output side a measured current $i_{GAS}$ flowing into the counter electrode 23 then occurs, which is approximately proportional to a gas concentration GAS of the gas to be detected. In principle this measured current $i_{GAS}$ can be captured using a current measurement device. The current value range is in this case typically measured in micro- and nano-amperes and is consequently metrologically difficult to capture.

In the example of the present FIG. 1 the apparatus already has, for the purpose of simplified and simultaneously improved capture of the measured current $i_{GAS}$, a transimpedance amplifier 4 for converting the measured current $i_{GAS}$ into a measured voltage $U_{GAS}$ proportional thereto. The measured voltage $U_{GAS}$ here represents the gas concentration GAS of the gas to be detected. The transimpedance amplifier 4 known per se has, for the impedance conversion and measured signal amplification, a series of electrical components, e.g. two resistors 42, 43 and a capacitor 44, for the appropriate wiring of another operation amplifier 41 for the technical implementation of the transimpedance amplification. In this case the voltage dropping at the resistor 42 and proportional to the measured current $i_{GAS}$ flowing through is amplified. The actual amplified measured signal is then applied as a measured voltage $U_{GAS}$ at the output of the operation amplifier 41. The reference character 45 further designates a reference voltage source for adjusting an offset voltage $U_{OFF}$, in order to enable an optimum working point for the operation of the electrolytic gas sensor 2.

Furthermore, the apparatus 1 has an electronic processing unit 5 with an analog measurement capture unit 51. The latter is set up to capture the measured current $i_{GAS}$ flowing into the counter electrode 23 or to capture the measured voltage $U_{GAS}$ already converted by means of the transimpedance amplifier 4. According to the invention the processing unit 5 or the analog measurement capture unit 51 is set up to capture a working, counter and reference voltage $U_A$, $U_G$, $U_R$ present in each case at the three electrodes 21-23 and in each case to monitor it for an impermissible deviation $\Delta U_A$, $\Delta U_G$, $\Delta U_R$, independently of the capture of the gas concentration GAS. In principle the measured voltage $U_{GAS}$ and the working, counter and reference voltages $U_A$, $U_G$, $U_R$ have a common reference potential GND. In other words, the above-mentioned voltages $U_{GAS}$, $U_A$, $U_G$, $U_R$ are all related to a common potential, typically to the same ground, e.g. the ground potential.

The analog measurement capture unit 51 can be implemented from several window comparators for the detection of the respective impermissible deviation $\Delta U_A$, $\Delta U_G$, $\Delta U_R$ and if necessary by one or more downstream logic gates for outputting a digital signal for a corresponding assigned error message F. Moreover, it can be set to also monitor the measured voltage $U_{GAS}$ for an impermissible voltage deviation $\Delta U_{GAS}$ and in an impermissible case to output an assigned second error message FGAS.

The respective measured inputs are designated by A1 to A4. For example, in each case a window comparator can be provided for discrimination of the measured voltage $U_{GAS}$ and the electrode voltages $U_A$, $U_G$, $U_R$. A window comparator can be implemented e.g. by two operation amplifiers wired as comparators with corresponding resistance wiring.

The processing unit 5 or the analog measurement capture unit 51 can moreover be set up to output a warning or alarm message WARN, AL if the measured voltage $U_{GAS}$ representing the gas concentration GAS exceeds a predefined threshold value or a threshold value which is time-dependent on the gas concentration GAS. In this case too, the analog measurement capture unit 51 can have one or more window comparators and analog time elements and if necessary one or more downstream logic gates for the digital output of the warning or alarm message WARN, AL.

Further, the processing unit 5 or the analog measurement capture unit 51 can be set up to monitor at least one combination of the measurement, working, counter and reference voltages $U_{GAS}$, $U_A$, $U_G$, $U_R$ in each case for another impermissible deviation and then in an impermissible case to output an assigned third error message. A possible combination can e.g. be the difference between or the sum of in each case two of the above-mentioned voltages $U_{GAS}$, $U_A$, $U_G$, $U_R$. The technical implementation can take place with the help of window comparators and with analog adders and subtractors and if necessary other downstream logic gates.

Finally the apparatus 1 shown can have a low-pass smoke filter 46 for filtering the measured voltage $U_{GAS}$. Preferably the edge frequency of the smoke filter 46 lies in a range between 0.1 and 10 Hertz. The low-pass smoke filter 46 shown is implemented e.g. as a first-order RC filter.

Figure 2:
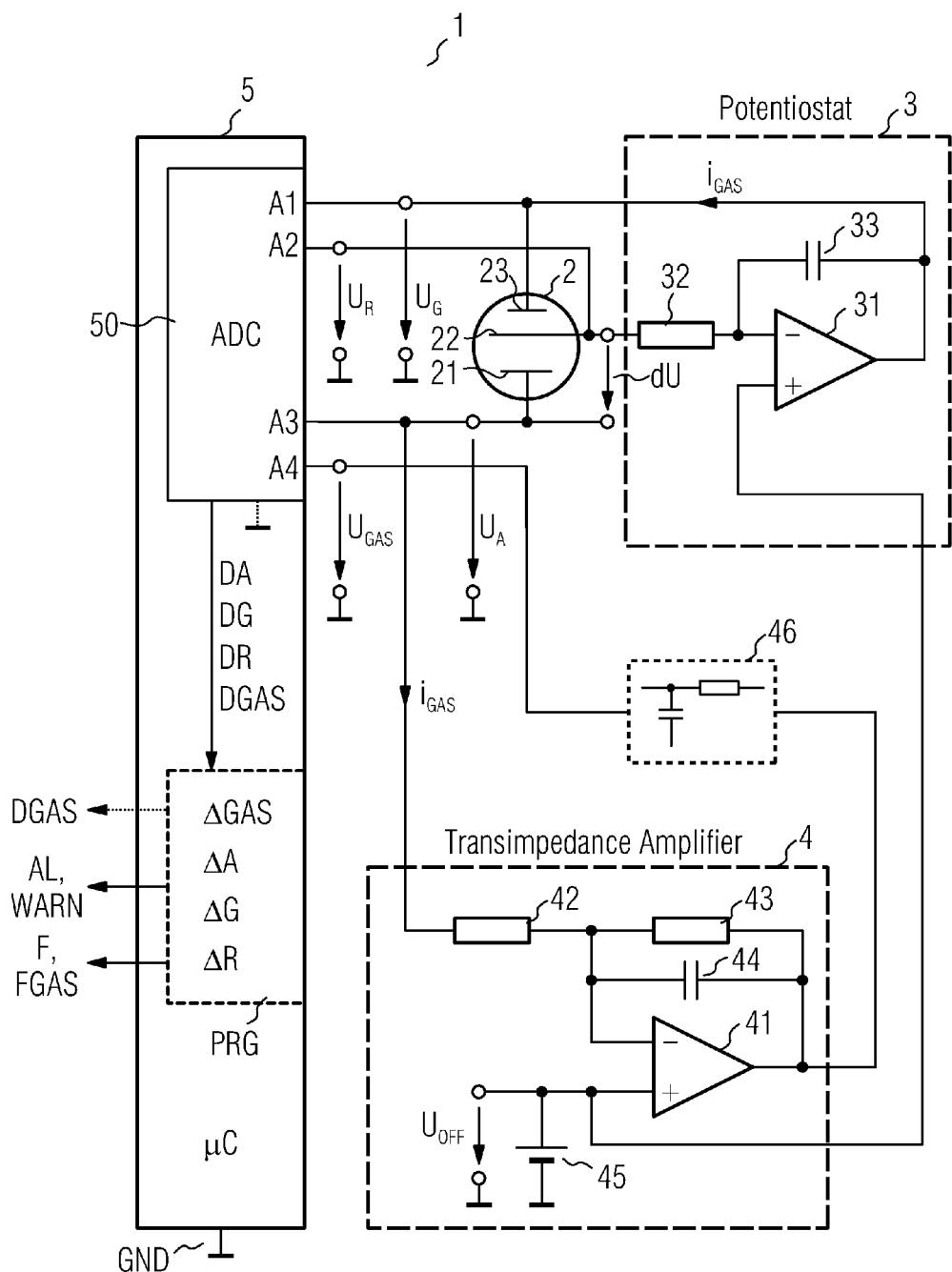
FIG. 2 is a schematic of an embodiment of the apparatus according to FIG. 1 according to the invention.

FIG. 2 shows an embodiment of the apparatus 1 according to FIG. 1 according to the invention. The apparatus 1 according to FIG. 2 differs from the apparatus 1 according to FIG. 1 in that the processing unit 5 has an A/D converter 50 for converting the measured voltage $U_{GAS}$ and the working, counter and reference voltages $U_A$, $U_G$, $U_R$ into corresponding digital values DGAS, DA, DG, DR. The processing unit 5 is preferably a microcontroller, which already has an integrated A/D converter 50. In the present example the A/D converter 50 shown has four analog measurement channels A1 to A4. Furthermore, the microcontroller 5 is set up to monitor the digital values DGAS, DA, DG, DR provided by the A/D converter 50 in each case for a digital value DGAS, DA, DG, DR corresponding to the impermissible deviation $\Delta U_{GAS}$, $\Delta U_A$, $\Delta U_G$, $\Delta U_R$ and in an impermissible case to output the respective assigned error message F, FGAS. This is preferably achieved by a suitable computer program PRG, which is stored in a memory of the microcontroller 5 or is loaded therefrom externally, and which is then executed by the microcontroller.

In addition, the microcontroller 5 can be set up or can have a suitable (further) computer program PRG in order to output a warning or alarm message WARN, AL if a respective determined gas concentration GAS exceeds a predefined threshold value or a threshold value which is time-dependent on the respective gas concentration GAS. For example, as the gas concentration GAS increases one or more preliminary warning messages WARN can also be output before the output of the alarm message AL. Finally, the microcontroller 5 can be set up to output an error message F, FGAS if it is established that the respective gas sensor 2 to be monitored is malfunctioning.

Figure 3:
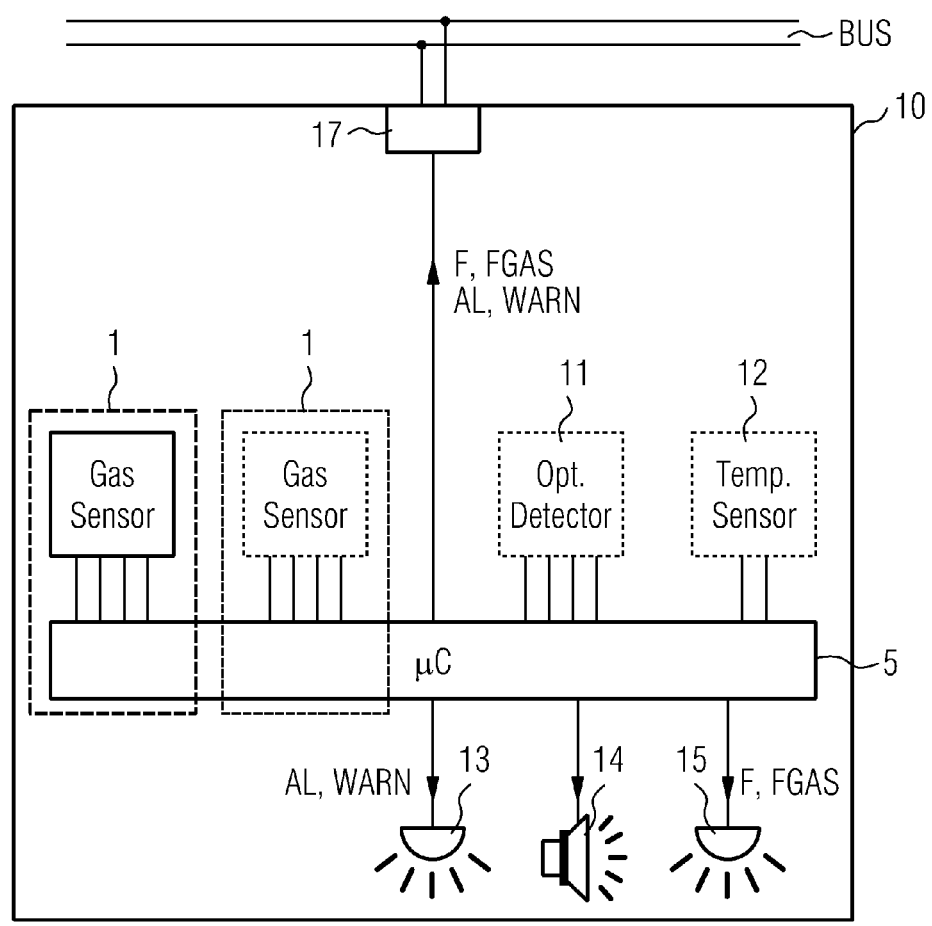
FIG. 3 is a diagrammatic view of an exemplary hazard alarm having two gas sensors, an optical detector, a temperature sensor and in each case an apparatus for the functional monitoring of the gas sensors according to the invention.

FIG. 3 shows by way of example a hazard alarm 10 having two gas sensors 2, an optical detector 11, a temperature sensor 12 and in each case an apparatus 1 for the functional monitoring of the gas sensors 2 according to the invention.

The hazard alarm 10 shown can also be called a multicriteria alarm, whereby for the detection of a hazard, e.g. a fire, several metrologically captured input variables can be combined with one another in order to increase the reliability of hazard detection and to minimize false alarms.

The hazard alarm 10 has a bus interface 17 for the possible output of the determined errors or error messages F, FGAS and of the warning and alarm messages WARN, AL to a connected alarm bus BUS. The alarm bus BUS is typically connected to a hazard alarm unit for processing of the incoming messages F, FGAS, AL, WARN and for initiation of corresponding countermeasures. The countermeasures can be e.g. the forwarding of a reported gas alarm to the fire department or the request to the service personnel for the hazard alarm reported as malfunctioning to be replaced.

Alternatively or additionally the output of the above-mentioned warning and alarm messages WARN, AL can take place to an optical output unit 13, e.g. to a flashing light, and/or to an acoustic output unit 14, e.g. to a sounder or buzzer. In the present example the hazard alarm 10 has another optical output unit 15, e.g. an LED, for outputting the error message F, FGAS. For example, a flashing red LED 15 can then inform a person present in the vicinity of the hazard alarm that it has been established that the hazard alarm 10 is malfunctioning.

In the present example the microcontroller 5 shown is set up simultaneously to control and check two inventive apparatuses 1 for the functional monitoring of the respective gas sensor and an optical detector 11 for smoke detection and a temperature detector 12 for detection of excess temperatures.

Figure 4:
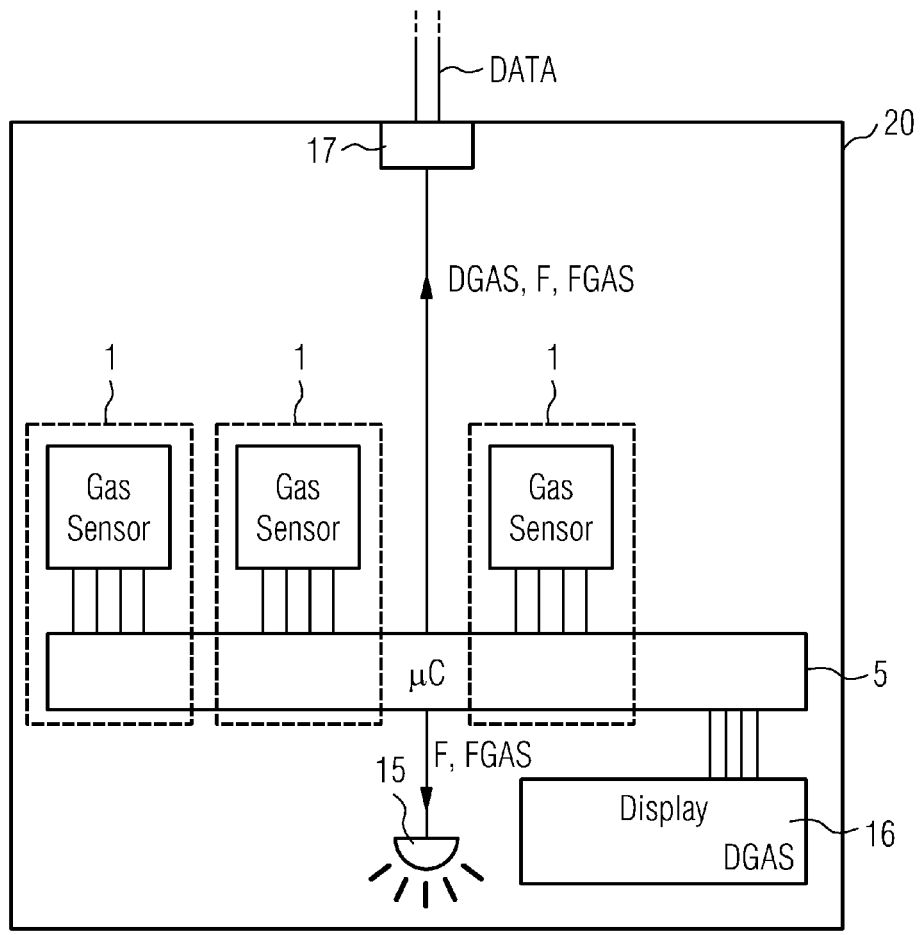
FIG. 4 is a diagram of an exemplary gas measurement device having three gas sensors, in each case with an apparatus for the functional monitoring of the gas sensors according to the invention, and FIG. 5 to FIG. 7 each shows a graph illustrating a functional failure of an electrolytic gas sensor and of detection using the inventive method.

FIG. 4 shows by way of example a gas measurement device 20 having three gas sensors 2 and in each case an apparatus 1 for the functional monitoring of the gas sensors 2 according to the invention.

The gas alarm 20 shown has a bus interface 17 for outputting the determined digital gas concentration values DGAS and for outputting any errors or error messages F, FGAS to a connected data bus DATA. Further gas alarms 20 or e.g. a measurement evaluation PC or a process control device can be connected to the latter.

Alternatively or additionally the output of the determined digital gas concentration values DGAS can take place on a display 16, e.g. on an LCD. Alternatively or additionally the output of the errors or error messages F, FGAS can furthermore take place to an optical output unit 15 and/or to the display 16. In the latter case concrete details of the determined errors F, FGAS can be output, e.g. "Failure of gas sensor 2: short circuit to ground detected!"

Figure 5:
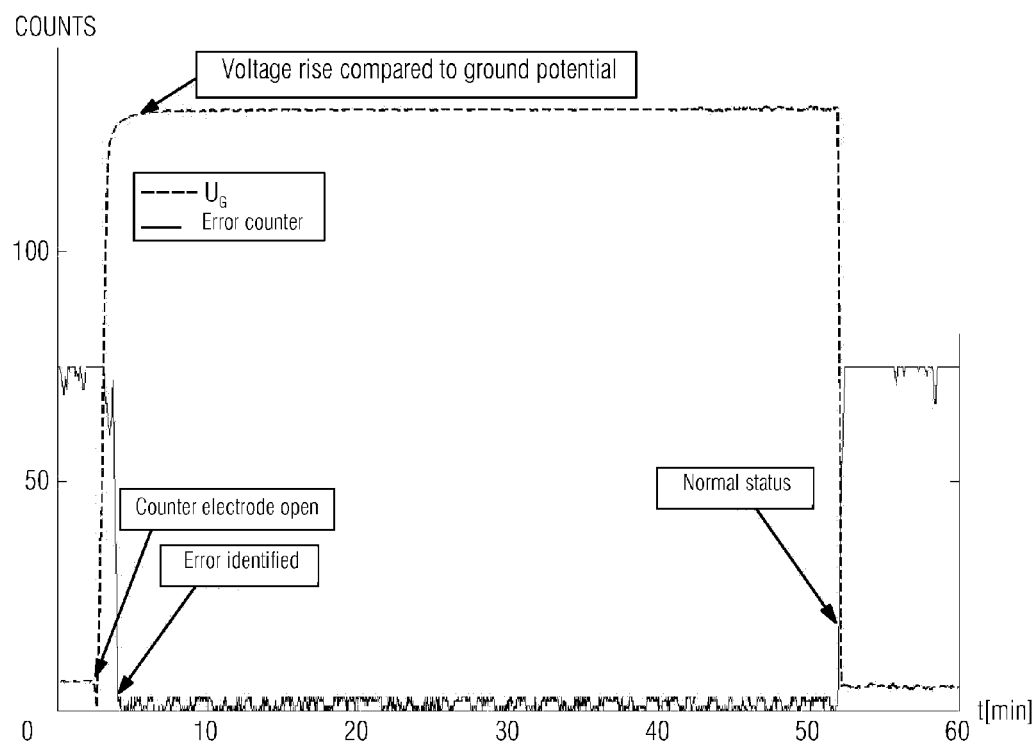

FIG. 5 shows the functional failure in the case of an erroneously open counter electrode of an electrolytic gas sensor and the detection thereof by the inventive method.

In the time diagram shown, so-called "counts" are plotted along the ordinate. These correspond to the respective digital value of the analog counter voltage $U_G$ entered using a dashed line and implemented by means of an ADC. The time is plotted in minutes along the abscissa. The development over time of the count status of an error counter is entered using a solid line. This is reduced by one count for each error plotted. When a count status is 0 an error is output. The adjustable "Decrement" allows errors occurring for a short time in the measurement chain not to contribute to the immediate triggering of an error, but for a certain predetermined number of error events to have to be reached first.

In normal error-free operating mode a differential voltage present between the reference and working electrodes is amplified and based on this the potential of the counter electrode is regulated such that this differential voltage becomes as small as possible. Thereupon a measured current which represents the gas concentration and flows into the counter electrode approximately proportionally to the gas concentration of the gas to be detected arises. According to the invention a working, counter and reference voltage present in each case at the three electrodes is now captured, independently of the determination of the measured current or of a measured current proportional thereto, and in each case is monitored for an impermissible deviation.

In the present case the counter voltage $U_G$ is monitored for an impermissible deviation compared to the ground potential, the counter voltage $U_G$ in normal error-free operating mode lying approximately on the $U_{off}$ potential. The impermissible deviation is evidenced in the example of the present figure by an abrupt rise in the counter voltage $U_G$. This error then typically becomes apparent when the electrical connection between the counter electrode and the ground potential is interrupted, i.e. open. This impermissible case is then output as an assigned error message. The right-hand end of FIG. 5 again shows the correct functioning of the gas sensor.

Figure 6:
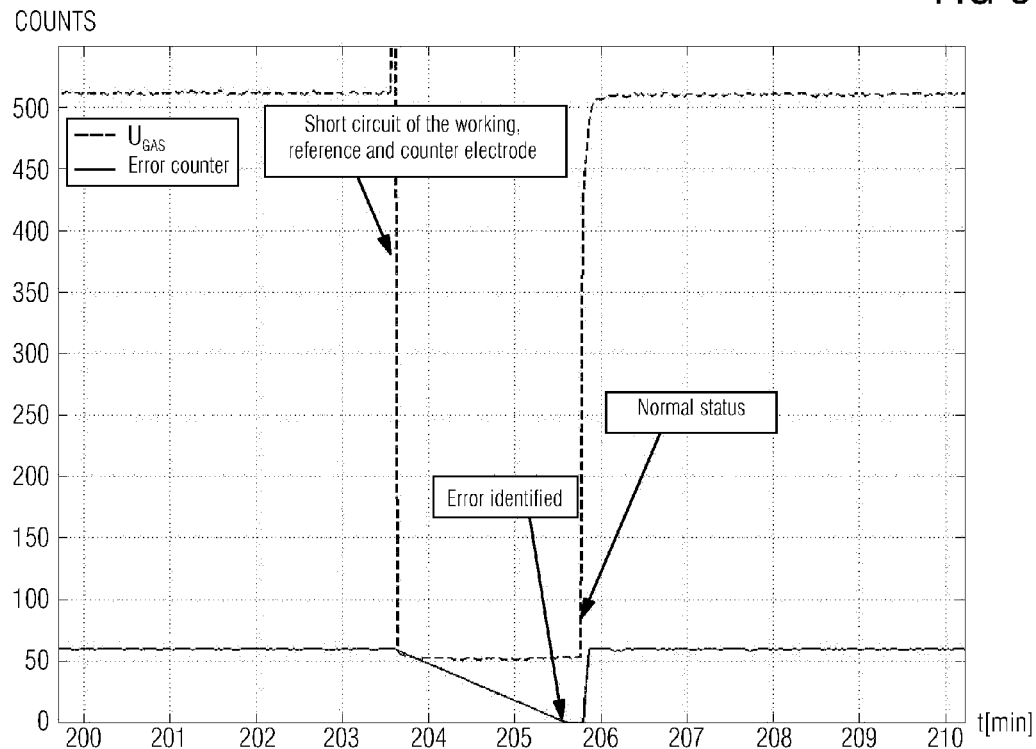

FIG. 6 shows the development over time of a functional failure in the case of a defective short circuit of the working, reference and counter electrodes with one another (no short circuit to ground) and the detection thereof by the inventive method. In this case the measured voltage $U_{GAS}$ corresponding to a current gas concentration occurs abruptly. Such signal behavior is however not plausible compared to a maximum signal change which can be output by the sensor, and nor can it be explained physically at all. This impermissible change in the measured voltage $U_G$ is then output as a second error message. In the present example this is the case if the error counter has again decremented to the value 0.

Figure 7:
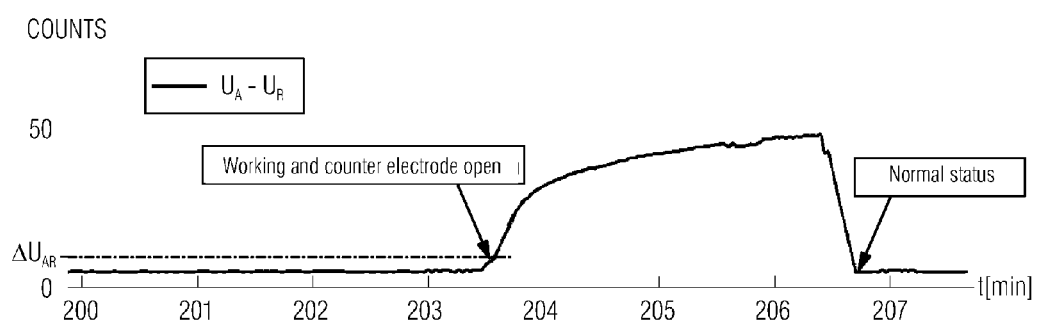

FIG. 7 shows by way of example a functional failure of an electrolytic gas sensor in the event of an impermissible deviation in the voltage difference between working voltage and reference voltage as at least one combination of the measurement, working, counter and reference voltages. In this case an assigned third error message is output.

Further unambiguously detectable error cases are described below:

Interruption of the counter electrode:
    The counter voltage $U_G$ changes abruptly for extreme voltage values with a sensor response time speed which cannot be explained.

Interruption of the reference electrode, of the counter and reference electrodes, of the counter and working electrodes, of the working and reference electrodes or of the working, reference and counter electrodes:
    The voltage differences from counter and reference voltage $U_G-U_R$ and from working and reference voltage $U_A-U_R$ drift outside defined limit values, which are not departed from in normal operation.

Interruption of the working electrode:
    The measured voltage $U_{GAS}$ is brought into line with the offset voltage $U_{OFF}$. The digital values corresponding to the offset voltage $U_{OFF}$ can be stored in the microcontroller, e.g. for monitoring.

Short circuit of the working and reference electrodes with one another, of the working and counter electrodes with one another and of all electrodes with one another (no short circuit to ground):
    The measured voltage $U_{GAS}$ drops to extreme voltage values below the offset voltage $U_{OFF}$, which is not possible in normal operation.

Short circuit in the counter and reference electrodes with one another (no short circuit to ground):
    The measured voltage $U_{GAS}$ briefly jumps to extreme, non-plausible values and then recovers.

Short circuit of individual, two or all electrodes with ground potential (short circuit to ground):
    This results in impermissibly high power consumption by the gas sensor, so that the hazard alarm or the gas measurement device signs off. In this case the gas sensor can no longer be supplied with sufficient current for normal measurement operation. Alternatively or additionally a further, fourth error message can be output.

The following is a summary list of reference numerals and the corresponding structure used in the above description of the invention:

1 Apparatus for functional monitoring
2 Gas sensor, electrolytic gas sensor
3 Potentiostat
4 Transimpedance amplifier
5 Electronic processing unit, microcontroller
10 Hazard alarm, gas alarm, smoke gas alarm, fire alarm
11 Optical detection unit
12 Temperature detection unit
13 Optical output unit, flashing light
14 Acoustic output unit, sounder, siren
15 Optical output unit, LED
16 Display, display unit
17 Interface, bus interface
20 Gas measurement device
21 Working electrode
22 Reference electrode
23 Counter electrode
31, 41 Operation amplifier
32, 42, 43 Ohmic resistance
33, 44 Capacitor, capacity
45 Reference voltage source
46 Low-pass filter, smoke filter
50 ADC, analog/digital converter
51 Analog measurement capture unit
A1-A4 Analog entries
AL Alarm signal, alarm message
BUS Alarm line, alarm bus, alarm loop
COUNTS Error counters
dU Differential voltage
DA, DG, Digital values of the electrode voltages
DATA DR Data cable, bus cable
DGAS Digital value of the measured voltage
$\Delta U_A, \Delta U_R, \Delta U_G, \Delta U_{GAS}, \Delta U_{AR}$ Deviation
$\Delta A, \Delta G,$ Digital value of the deviation
$\Delta R, \Delta GAS$ Digital value of the deviations
F, FGAS Error signal, error message
GAS Gas concentration
GND Reference potential, ground, ground potential
$i_{GAS}$ Measured current
PRG Program, computer program
t Time
$U_A$ Working voltage
$U_R$ Reference voltage
$U_G$ Counter voltage
$U_{GAS}$ Measured voltage
$U_{OFF}$ Offset voltage
WARN Warning signal, warning message

The invention claimed is:

1. A method for the functional monitoring of an electrolytic gas sensor that is sensitive to a specific gas, the gas sensor having a working electrode, a reference electrode, and a counter electrode, the method comprising:
    amplifying a differential voltage present between the reference and working electrodes and regulating the differential voltage on a basis of a potential of the counter electrode such that the differential voltage becomes as small as possible, whereupon a measured current arises which flows into the counter electrode and is approximately proportional to a gas concentration of the gas to be detected;
    converting the measured current into a measured voltage proportional thereto, wherein then the measured voltage represents the gas concentration approximately proportional thereto; and
    independently of a determination of the measured current representing the gas concentration, capturing a working voltage present at the working electrode, a counter voltage present at the counter electrode, and a reference voltage present at the reference electrode and monitoring the voltages for an impermissible deviation;
    when an impermissible deviation is detected, outputting an assigned error message; and
    monitoring at least one combination of the measurement voltage, the working voltage, the counter voltage and the reference voltage for another impermissible deviation and, in an impermissible case, outputting an assigned further error message.

2. The method according to claim 1, which comprises outputting a warning or alarm message if the measured voltage representing the gas concentration exceeds or undershoots a predefined threshold value or a threshold value which is time-dependent on the gas concentration.

3. The method according to claim 1, which comprises monitoring the measured voltage for an impermissible voltage deviation and, in an impermissible case, outputting an assigned other error message.

4. An apparatus for the functional monitoring of an electrolytic gas sensor that is sensitive to a specific gas and that has three electrodes including a working electrode, a reference electrode, and a counter electrode, the apparatus comprising:
   a potentiostat for amplifying a differential voltage present between the reference and working electrodes and for regulating a potential of the counter electrode so that the differential voltage becomes as small as possible; and
   an electronic processing unit configured to capture a measured current that flows into the counter electrode and that is approximately proportional to a gas concentration of the gas to be detected;
   a transimpedance amplifier for converting the measured current into a measured voltage proportional thereto and said electronic processing unit for capturing the measured voltage then representing the gas concentration;
   said electronic processing unit being further configured, independently of determining the gas concentration, to capture a working voltage, a counter voltage, and a reference voltage respectively present at the three electrodes, in each case to monitor the respective voltage for an impermissible deviation and, in an impermissible case, to output an assigned error message; and
   said electronic processing unit being configured to monitor at least one combination of digital values corresponding to two of the measurement, working, counter and reference voltages in each case for another impermissible deviation and in an impermissible case to output same to an assigned further error message.

5. The apparatus according to claim 4, wherein said electronic processing unit is set up to monitor the measured voltage for an impermissible voltage deviation and in an impermissible case to output an assigned other error message.

6. The apparatus according to claim 4, wherein the measured voltage and the working, counter and reference voltages have a common reference potential.

7. The apparatus according to claim 4, wherein said processing unit comprises an A/D converter for converting the measured voltage and the working, counter and reference voltages into corresponding digital values or said processing unit is connected to an A/D converter by way of a data communications link, and wherein said processing unit is configured to monitor the digital values in each case for a digital value corresponding to the impermissible deviation and in an impermissible case to output the respective assigned error message.

8. The apparatus according to claim 7, wherein the measured voltage and the working, counter and reference voltages are convertable by way of said A/D converter into the corresponding digital values substantially simultaneously, with a scanning rate in a range between 0.25 and 4 Hertz.

9. The apparatus according to claim 4, comprising a low-pass smoke filter upstream of an A/D converter for filtering the measured voltage with an edge frequency of less than 10 Hertz.

10. The apparatus according to claim 9, wherein the edge frequency is less than 1 Hertz.

11. A hazard alarm system, comprising:
   at least one electrolytic gas sensor that is sensitive to a specific gas;
   an apparatus according to claim 4 for the functional monitoring of the respective gas sensor;
   a first output unit for outputting a warning or alarm message if a respective determined gas concentration exceeds or undershoots a predefined threshold value or a threshold value which is time-dependent on the respective gas concentration; and
   a second output unit for outputting an error message if a malfunction of the respective gas sensor is determined.

12. A gas measuring device, comprising:
   at least one electrolytic gas sensor that is sensitive to a specific gas;
   an apparatus according to claim 4 for the functional monitoring of said at least one gas sensor;
   a measurement output unit for outputting a respective gas concentration; and
   a further output unit for outputting an error message if a malfunction of said at least one gas sensor is determined.

* * * * *